US009592501B2

(12) United States Patent
Jarvius et al.

(10) Patent No.: US 9,592,501 B2
(45) Date of Patent: Mar. 14, 2017

(54) MICROFLUIDIC STRUCTURE

(71) Applicant: Landegren Gene Technology AB, Uppsala (SE)

(72) Inventors: Jonas Sven Peter Jarvius, Uppsala (SE); Jonas Melin, Uppsala (SE)

(73) Assignee: LANDEGREN GENE TECHNOLOGY AB, Uppsala (SE)

(*) Notice: Subject to any disclaimer, the term of this patent is extended or adjusted under 35 U.S.C. 154(b) by 0 days.

(21) Appl. No.: 14/963,864

(22) Filed: Dec. 9, 2015

(65) Prior Publication Data
US 2016/0096176 A1    Apr. 7, 2016

Related U.S. Application Data

(63) Continuation of application No. 11/576,182, filed as application No. PCT/GB2005/003736 on Sep. 28, 2005, now abandoned.

(30) Foreign Application Priority Data

Sep. 28, 2004   (GB) .................................. 0421529.9

(51) Int. Cl.
| B01L 3/00 | (2006.01) |
| C23C 16/48 | (2006.01) |
| C12M 3/06 | (2006.01) |
| C23C 16/22 | (2006.01) |
| B29C 65/00 | (2006.01) |
| B81B 1/00 | (2006.01) |
| F04B 43/04 | (2006.01) |
| F04B 43/06 | (2006.01) |
| G01N 27/447 | (2006.01) |
| B29L 31/00 | (2006.01) |

(52) U.S. Cl.
CPC ... *B01L 3/502707* (2013.01); *B01L 3/502738* (2013.01); *B01L 3/502746* (2013.01); *B29C 65/002* (2013.01); *B29C 65/006* (2013.01); *B29C 66/026* (2013.01); *B29C 66/53461* (2013.01); *B29C 66/5412* (2013.01); *B81B 1/00* (2013.01); *C12M 23/16* (2013.01); *C23C 16/22* (2013.01); *C23C 16/487* (2013.01); *F04B 43/043* (2013.01); *F04B 43/06* (2013.01); *G01N 27/44791* (2013.01); *B01L 2200/12* (2013.01); *B01L 2300/0806* (2013.01); *B01L 2300/0816* (2013.01); *B01L 2300/0887* (2013.01); *B01L 2300/12* (2013.01); *B29L 2031/756* (2013.01); *Y10T 29/49229* (2015.01)

(58) Field of Classification Search
None
See application file for complete search history.

(56) References Cited

U.S. PATENT DOCUMENTS

| 5,647,939 | A | 7/1997 | Gee et al. |
| 5,922,591 | A | 7/1999 | Anderson et al. |
| 6,153,389 | A | 11/2000 | Haarer et al. |
| 6,176,962 | B1 | 1/2001 | Soane et al. |
| 6,197,595 | B1 | 3/2001 | Anderson et al. |
| 6,432,290 | B1 | 8/2002 | Harrison et al. |
| 6,461,492 | B1 | 10/2002 | Hayashizaki et al. |
| 6,623,613 | B1 | 9/2003 | Mathies et al. |
| 6,719,868 | B1 | 4/2004 | Schueller et al. |
| 6,740,219 | B2 | 5/2004 | Imai et al. |
| 7,005,052 | B2 | 2/2006 | Shimizu et al. |
| 7,097,809 | B2 | 8/2006 | Van Dam et al. |
| 7,142,987 | B2 | 11/2006 | Eggers |
| 7,312,611 | B1 | 12/2007 | Harrison et al. |
| 7,419,639 | B2 | 9/2008 | Osterfeld et al. |
| 7,445,926 | B2 | 11/2008 | Mathies et al. |
| 7,584,240 | B2 | 9/2009 | Eggers |
| 7,589,184 | B2 | 9/2009 | Hogan et al. |
| 7,718,442 | B2 | 5/2010 | Davis et al. |
| 7,745,207 | B2 | 6/2010 | Jovanovich et al. |
| 7,749,365 | B2 | 7/2010 | Nguyen et al. |
| 7,763,453 | B2 | 7/2010 | Clemmens et al. |

(Continued)

FOREIGN PATENT DOCUMENTS

| EP | 0797529 A1 | 10/1997 |
| EP | 2096445 B1 | 6/2014 |
| JP | 2001305050 A | 10/2001 |
| JP | 2002055098 A | 2/2002 |
| JP | 2004138411 A | 5/2004 |
| JP | 2005305234 A | 11/2005 |
| WO | WO-9618550 A1 | 6/1996 |
| WO | WO-0243615 A2 | 6/2002 |
| WO | WO-2004020065 A2 | 3/2004 |
| WO | WO-2008065868 A1 | 6/2008 |

(Continued)

OTHER PUBLICATIONS

Melin et al., "Thermoplastic Microfluidic Platform for Single-Molecule Detection, Cell Culture, and Actuation," Anal. Chem., 2005, vol. 77, No. 22, pp. 7122-7130, Publication Date (Web): Oct. 8, 2005.*

(Continued)

*Primary Examiner* — Galina Yakovleva
(74) *Attorney, Agent, or Firm* — Wilson Sonsini Goodrich & Rosati

(57) ABSTRACT

A microfluidic structure comprising a thermoplastic portion defining a microfluidic recess, a bonding layer on the thermoplastic portion and a siloxane elastomer portion covalently bonded to the bonding layer to seal the microfluidic recess. The microfluidic recess can therefore be formed simply, quickly and cheaply using known injection molding techniques, which are not hampered by the need for a curing step. However, the positive qualities associated with elastomers can be brought to the structure by using this to seal the microchannels. The bonding layer can be formed by silica deposited on the thermoplastic portion using techniques known in the field of optics.

19 Claims, 8 Drawing Sheets

(56) References Cited

U.S. PATENT DOCUMENTS

| | | |
|---|---|---|
| 7,766,033 B2 | 8/2010 | Mathies et al. |
| 7,785,458 B2 | 8/2010 | Shimizu et al. |
| 7,803,281 B2 | 9/2010 | Davies et al. |
| 8,034,628 B2 | 10/2011 | Harrison et al. |
| RE43,122 E | 1/2012 | Harrison et al. |
| 8,142,635 B2 | 3/2012 | Shimizu et al. |
| 8,283,165 B2 | 10/2012 | Hogan et al. |
| 8,388,908 B2 | 3/2013 | Blaga et al. |
| 8,394,642 B2 | 3/2013 | Jovanovich et al. |
| 8,431,340 B2 | 4/2013 | Jovanovich et al. |
| 8,431,384 B2 | 4/2013 | Hogan et al. |
| 8,431,390 B2 | 4/2013 | Jovanovich et al. |
| 8,476,063 B2 | 7/2013 | Jovanovich et al. |
| 8,512,538 B2 | 8/2013 | Majlof et al. |
| 8,551,714 B2 | 10/2013 | Jovanovich et al. |
| 8,557,518 B2 | 10/2013 | Jovanovich et al. |
| 8,562,918 B2 | 10/2013 | Jovanovich et al. |
| 8,584,703 B2 | 11/2013 | Kobrin et al. |
| 8,672,532 B2 | 3/2014 | Jovanovich et al. |
| 8,748,165 B2 | 6/2014 | Vangbo et al. |
| 8,763,642 B2 | 7/2014 | Vangbo |
| 8,841,116 B2 | 9/2014 | Mathies et al. |
| 8,894,946 B2 | 11/2014 | Nielsen et al. |
| 9,012,236 B2 | 4/2015 | Jovanovich et al. |
| 9,121,058 B2 | 9/2015 | Jovanovich et al. |
| 9,341,284 B2 | 5/2016 | Vangbo |
| 2003/0087425 A1 | 5/2003 | Eggers |
| 2003/0087446 A1 | 5/2003 | Eggers |
| 2003/0087455 A1 | 5/2003 | Eggers et al. |
| 2003/0088657 A1 | 5/2003 | Eggers |
| 2003/0129755 A1 | 7/2003 | Sadler et al. |
| 2003/0215369 A1 | 11/2003 | Eggers et al. |
| 2003/0217923 A1 | 11/2003 | Harrison et al. |
| 2004/0087033 A1 | 5/2004 | Schembri |
| 2004/0101966 A1 | 5/2004 | Davis et al. |
| 2004/0209354 A1 | 10/2004 | Mathies et al. |
| 2004/0219533 A1 | 11/2004 | Davis et al. |
| 2005/0026181 A1 | 2/2005 | Davis et al. |
| 2005/0042656 A1 | 2/2005 | Davis et al. |
| 2005/0224352 A1 | 10/2005 | Harrison et al. |
| 2005/0287572 A1 | 12/2005 | Mathies et al. |
| 2006/0014177 A1 | 1/2006 | Hogan et al. |
| 2006/0027456 A1 | 2/2006 | Harrison et al. |
| 2006/0073484 A1 | 4/2006 | Mathies et al. |
| 2006/0260941 A1 | 11/2006 | Tan et al. |
| 2007/0175756 A1 | 8/2007 | Nguyen et al. |
| 2007/0218485 A1 | 9/2007 | Davis et al. |
| 2007/0237686 A1 | 10/2007 | Mathies et al. |
| 2007/0248958 A1 | 10/2007 | Jovanovich et al. |
| 2008/0014576 A1 | 1/2008 | Jovanovich et al. |
| 2008/0237146 A1 | 10/2008 | Harrison et al. |
| 2008/0241844 A1 | 10/2008 | Kellogg |
| 2008/0311585 A1 | 12/2008 | Gao et al. |
| 2009/0020427 A1 | 1/2009 | Tan et al. |
| 2009/0023603 A1 | 1/2009 | Selden et al. |
| 2009/0035770 A1 | 2/2009 | Mathies et al. |
| 2009/0056822 A1 | 3/2009 | Young et al. |
| 2009/0060797 A1 | 3/2009 | Mathies et al. |
| 2009/0084679 A1 | 4/2009 | Harrison et al. |
| 2009/0178934 A1 | 7/2009 | Jarvius et al. |
| 2009/0253181 A1 | 10/2009 | Vangbo et al. |
| 2010/0068723 A1 | 3/2010 | Jovanovich et al. |
| 2010/0075858 A1 | 3/2010 | Davis et al. |
| 2010/0092948 A1 | 4/2010 | Davis et al. |
| 2010/0111770 A1 | 5/2010 | Hwang et al. |
| 2010/0165784 A1 | 7/2010 | Jovanovich et al. |
| 2010/0172898 A1 | 7/2010 | Doyle et al. |
| 2010/0173392 A1 | 7/2010 | Davis et al. |
| 2010/0173398 A1 | 7/2010 | Peterman |
| 2010/0178210 A1 | 7/2010 | Hogan et al. |
| 2010/0209957 A1 | 8/2010 | Hogan et al. |
| 2010/0218623 A1 | 9/2010 | Eggers et al. |
| 2010/0221726 A1 | 9/2010 | Zenhausern et al. |
| 2010/0228513 A1 | 9/2010 | Roth et al. |
| 2010/0248363 A1 | 9/2010 | Hogan et al. |
| 2010/0266432 A1 | 10/2010 | Pirk et al. |
| 2010/0285578 A1 | 11/2010 | Selden et al. |
| 2010/0285975 A1 | 11/2010 | Mathies et al. |
| 2010/0326826 A1 | 12/2010 | Harrison et al. |
| 2011/0005932 A1 | 1/2011 | Jovanovich et al. |
| 2011/0008785 A1 | 1/2011 | Tan et al. |
| 2011/0039303 A1 | 2/2011 | Jovanovich et al. |
| 2011/0048945 A1 | 3/2011 | Harrison et al. |
| 2011/0053784 A1 | 3/2011 | Unger et al. |
| 2011/0076735 A1 | 3/2011 | Jovanovich et al. |
| 2011/0124049 A1 | 5/2011 | Li et al. |
| 2011/0126911 A1 | 6/2011 | Kobrin et al. |
| 2011/0126179 A1 | 6/2011 | Bin/Lee et al. |
| 2011/0137018 A1 | 6/2011 | Chang-Yen et al. |
| 2011/0171086 A1 | 7/2011 | Prins et al. |
| 2011/0189678 A1 | 8/2011 | McBride et al. |
| 2011/0195495 A1 | 8/2011 | Selden et al. |
| 2011/0212440 A1 | 9/2011 | Viovy et al. |
| 2011/0229897 A1 | 9/2011 | Bell et al. |
| 2011/0229898 A1 | 9/2011 | Bell et al. |
| 2011/0240127 A1 | 10/2011 | Eberhart et al. |
| 2011/0256530 A1 | 10/2011 | Hogan |
| 2011/0290648 A1 | 12/2011 | Majlof et al. |
| 2011/0312614 A1 | 12/2011 | Selden et al. |
| 2012/0088249 A1 | 4/2012 | Jovanovich et al. |
| 2012/0100522 A1 | 4/2012 | Saghbini et al. |
| 2012/0115189 A1 | 5/2012 | Jovanovich et al. |
| 2012/0164036 A1 | 6/2012 | Stern et al. |
| 2012/0181460 A1 | 7/2012 | Eberhart et al. |
| 2012/0267247 A1 | 10/2012 | Tan et al. |
| 2012/0308987 A1 | 12/2012 | Hogan et al. |
| 2012/0315635 A1 | 12/2012 | Vangbo et al. |
| 2013/0029338 A1 | 1/2013 | Jovanovich et al. |
| 2013/0053255 A1 | 2/2013 | Vangbo et al. |
| 2013/0074944 A1 | 3/2013 | Van Gelder |
| 2013/0084565 A1 | 4/2013 | Landers et al. |
| 2013/0115607 A1 | 5/2013 | Nielsen et al. |
| 2013/0121892 A1 | 5/2013 | Fuhrmann et al. |
| 2013/0139895 A1 | 6/2013 | Vangbo |
| 2013/0203634 A1 | 8/2013 | Jovanovich et al. |
| 2013/0210129 A1 | 8/2013 | Selden et al. |
| 2013/0213810 A1 | 8/2013 | Tan et al. |
| 2013/0217026 A1 | 8/2013 | Egan et al. |
| 2013/0224846 A1 | 8/2013 | Jovanovich et al. |
| 2013/0344475 A1 | 12/2013 | Jovanovich et al. |
| 2014/0045704 A1 | 2/2014 | Jovanovich et al. |
| 2014/0065628 A1 | 3/2014 | Van Gelder et al. |
| 2014/0065689 A1 | 3/2014 | Hogan et al. |
| 2014/0370519 A1 | 12/2014 | Vangbo et al. |
| 2015/0021502 A1 | 1/2015 | Vangbo |
| 2015/0024436 A1 | 1/2015 | Eberhart et al. |
| 2015/0136602 A1 | 5/2015 | Jovanovich |
| 2015/0136604 A1 | 5/2015 | Nielsen |
| 2016/0016140 A1 | 1/2016 | Jovanovich et al. |
| 2016/0053314 A1 | 2/2016 | Jovanovich et al. |
| 2016/0116439 A1 | 4/2016 | Kindwall et al. |

FOREIGN PATENT DOCUMENTS

| | | |
|---|---|---|
| WO | WO-2009129415 A1 | 10/2009 |
| WO | WO-2010041174 A1 | 4/2010 |
| WO | WO-2010130762 A2 | 11/2010 |
| WO | WO-2011012621 A1 | 2/2011 |
| WO | WO-2011056215 A1 | 5/2011 |
| WO | WO-2011084703 A2 | 7/2011 |

OTHER PUBLICATIONS

Melin et al., "A novel microfluidic platform design combining actuators, cell culture and sensitive fluorescence detection with disposable microchips," Microtas, Sep. 13, 2004, vol. 2, pp. 551-553.*

Barker, et al. Plastic Microfluidic Devices Modified with Polyelectrolyte Multilayers. Anal. Chem., 2000, 72 (20), pp. 4899-4903.

Becker, et al. "Polymer microfluidic devices," Talanta, 2002, vol. 56, issue 2, pp. 267-287.

(56) References Cited

OTHER PUBLICATIONS

Co-pending U.S. Appl. No. 14/032,173, filed Sep. 10, 2013.
Co-pending U.S. Appl. No. 14/474,047, filed Aug. 29, 2014.
Co-pending U.S. Appl. No. 14/659,108, filed Mar. 16, 2015.
Co-pending U.S. Appl. No. 14/824,333, filed Aug. 12, 2015.
Co-pending U.S. Appl. No. 14/919,620, filed Oct. 21, 2015.
Co-pending U.S. Appl. No. 12/026,510, filed Feb. 5, 2008.
Dreuth, et al., "A method for local application of thin organic adhesive films on micropatterned structures", Materials Science and Engineering C 5 (1998) pp. 227-231.
Duffy, et al. Rapid Prototyping of Microfluidic Systems in Poly(dimethylsiloxane). Anal. Chem. 1998; 4974-4984.
Fu, et al. An Integrated Microfabricated Cell Sorter, Analytical Chemistry, vol. 74, No. 11, pp. 2451-2457.
Hong, et al., "A Nanoliter-scale nucleic acid processor with parallel architecture", Nature Biotechnology, vol. 22, No. 4, Apr. 2004, pp. 435-439.
Hong, et al., "Integrated nanoliter systems", Nature Biotechnology, vol. 21, No. 10, Oct. 2003, pp. 1179-1183.
International preliminary report on patentability with search report and written opinion dated Apr. 3, 2007 for PCT Application No. PCT/GB2005/003736.
Kim, et al., "A disposable polydimethylsiloxane-based diffuser micropump actuated by piezoelectric-disc", Microelectronic Engineering 71 (2004) pp. 119-124.
Kwok, et al. Velocity Measurement of Particles Flowing in a Microfluidic Chip Using Shah Convolution Fourier Transform Detection. Anal Chem., 2001, 73 (8), pp. 1748-1753.
Leclerc, et al. "Cell Culture in 3-Dimensional Microfluidic Structure of PDMS (polydimethylsiloxane)" Biomedical Microdevices 5:2, (2003), pp. 109-114.
Lee, et al., "Design and Fabrication of CD-Like Microfluidic Platforms for Diagnostics: Polymer-Based Microfabrication", Biomedical Microdevices 3:4, pp. 339-351, 2001.

McDonald, et al., "Poly(dimethylsiloxane) as a Material for Fabricating Microfluidic Devices", Accounts of Chemical Research, vol. 35, No. 7, 2002, pp. 491-499.
Merkel, et al. "Gas sorption, diffusion, and permeation in poly (dimethylsiloxane)."*Journal of Polymer Science Part B: Polymer Physics*38.3 (2000): 415-434.
Office action dated Jan. 6, 2012 for U.S. Appl. No. 11/576,182.
Office action dated Jan. 13, 2015 for U.S. Appl. No. 11/576,182.
Office action dated May 31, 2011 for U.S. Appl. No. 11/576,182.
Office action dated Jun. 25, 2014 for U.S. Appl. No. 11/576,182.
Ro, et al., "Poly(dimethylsiloxane) microchip for precolumn reaction and micellar electrokinetic chromatography of biogenic amines", Electrophoresis 2002, 23, pp. 1129-1137.
Rossier, et al., "Microchannel networks for electrophoretic separations", Electrophoresis 1999, vol. 20, pp. 727-731.
Sakai, et al. "Silica coating on plastics by liquid phase deposition (LPD) method," Thin Solid Films, 2001, vol. 392, issue 2, pp. 294-298.
Schift, et al., "Nanoreplication in polymers using hot embossing and injection molding", Microelectronic Engineering 53 (2000), pp. 171-174.
Schulz, et al., "Antireflection coating design for plastic optics," Applied Optics, 2002, vol. 41, issue 16, pp. 3107-3110.
Svedberg, et al., "Sheathless Electrospray from Polymer Microchips", Analytical Chemistry, vol. 75, No. 15, Aug. 1, 2003, pp. 3934-3940.
Thorsen, et al., "Microfluidic Large-Scale Integration", www.sciencemag.org, Science, vol. 298, Oct. 18, 2002, pp. 580-584.
Unger, et al. Monolithic microfabricated valves and pumps by multilayer soft lithography. Science. Apr. 7, 2000;288(5463):113-6.
Walker, et al., "Insect Cell Culture in Microfluidic Channels", Biomedical Microdevices 4:3, pp. 161-166 (2002).
Co-pending U.S. Appl. No. 15/037,039, filed on May 16, 2016.
Co-pending U.S. Appl. No. 15/117,053, filed on Aug. 5, 2016.
Co-pending U.S. Appl. No. 15/154,086, filed May 13, 2016.

\* cited by examiner

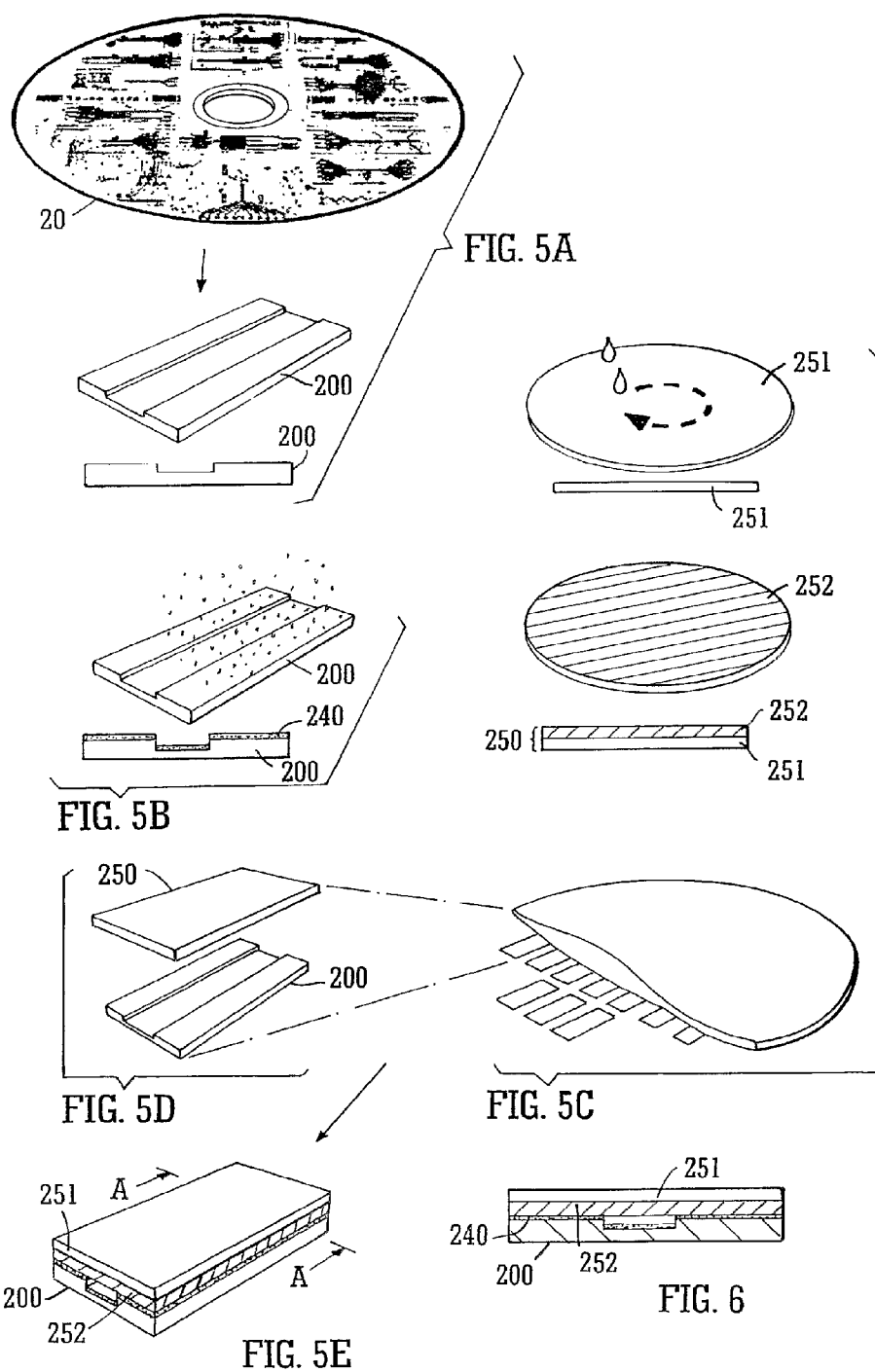

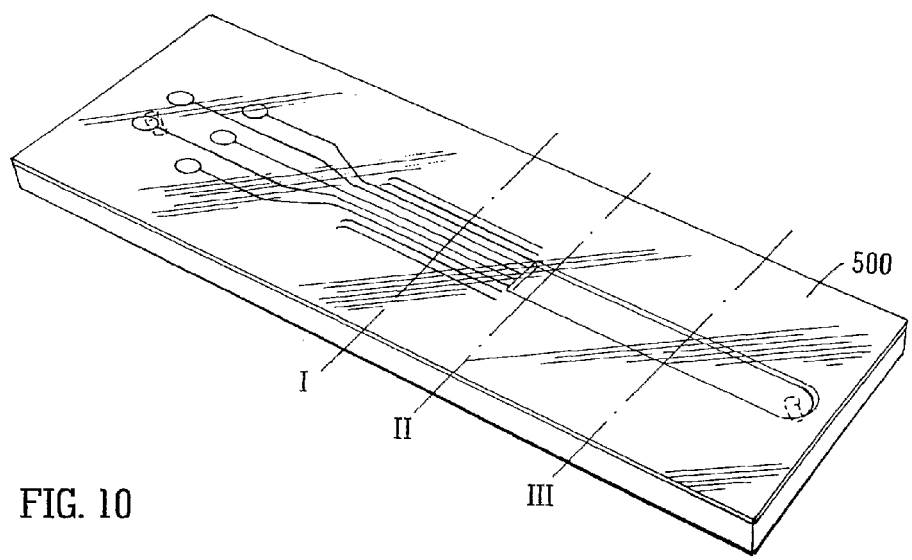
FIG. 10
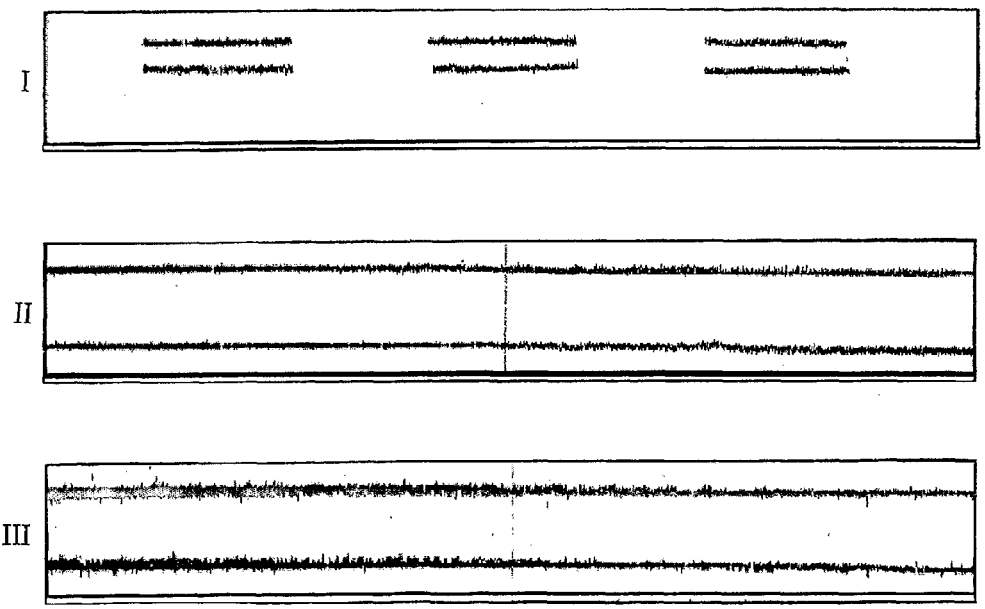

MICROFLUIDIC STRUCTURE

CROSS-REFERENCE

This application is a Continuation Application of U.S. patent application Ser. No. 11/576,182, filed Feb. 28, 2008, which is a National Stage Entry of International Patent Application No. PCT/GB2005/003736, filed Sep. 28, 2005, which claims priority to British Patent Application No. GB 0421529.9, filed Sep. 28, 2004, each of which is incorporated herein by reference in its entirety.

This invention relates to a microfluidic structure and a method for making such a structure.

BACKGROUND

Microfluidic structures allow liquid volumes to be manipulated on a very small scale, in the nanoliter range. This has many benefits for biological sampling and testing, such as the reduced consumption of samples and reagents, shorter analysis times, greater sensitivity and ease of transportation and disposal. Initially such systems were made using glass or silicon, as methods of manufacturing with these materials were known from the microelectronics industry. Channels were created by, e.g., photo lithography, wet etching or micromachining, after which the channels were sealed by a layer of the same material using anodic bonding, fusion bonding or adhesives.

However, glass and silicon are not best suited to the biomedical field as they are expensive, can lack optical clarity, have a low impact strength and poor biocompatibility. Therefore there has been a move away from these materials towards plastics. These offer a wide range of physical and chemical characteristics. A discussion of various methods of manufacture of polymer microfluidic devices can be found in Polymer Microfluidic Devices by Holger Becker and Laurie Locascio (Talanta 56 (2002) 267-287).

One of the methods discussed is that of injection moulding using compact disc (CD) manufacturing technology. Here a master is made from silicon using wet chemical etching or deep reactive ion etching. Nickel electroforms are then produced from the silicon master in order to transfer the micro features to a substrate suitable for injection moulding. The nickel electroform is then mounted onto a mould insert and thermoplastic resin is introduced to form the microchannels. These are later sealed to a polymer substrate of the same type or one with a lower glass transition temperature using low temperature thermal annealing.

Alternative ways of forming microchannels are by imprinting or hot embossing.

Recently elastomers have gained popularity in the field of microfluidic devices due to their flexibility. This allows channels in the elastomer to be closed by the application of pressure to the elastomer, which distorts the shape of the channels. By having a series of layered channels fluid movement in one channel can be controlled by the application of pressurised air to channels positioned above it. This allows microfluidic devices to be fashioned with inbuilt pumps or valves and allows the controlled dispensing or movement of fluid within the device. Poly(dimethylsiloxane) (PDMS) has emerged as a useful elastomer for rapid prototyping of microfluidic structures as it is inexpensive, easy to replicate by moulding and is optically transparent. In addition, PDMS has a high oxygen and carbon dioxide permeability which permits cells located in the microchannels to maintain aerobic metabolism. This is a major difference over conventional plastic, glass and silicon devices which do not allow for gas exchange and are therefore not suited for cell based applications.

WO02/43615 discloses several methods of manufacturing a microfluidic device Lasing elastomers, in particular PDMS.

First moulds are micromachined Lasing conventional techniques, e.g. photolithography, to create the microchannels in relief. Uncured elastomer is placed over the mould and allowed to cure to form microchannels. The elastomer can them be bonded to a substrate or to another piece of elastomer to seal the channels.

Several methods of bonding elastomer to elastomer are discussed, including a reference to Rapid Prototyping of Microfluidic Systems in Poly(dimethylsiloxane) by Duffy et al (Anal. Chem. 1998, 70, 4974-4984). This discloses a method for making PDMS microfluidic systems by first creating a master by photolithography of a silicon wafer. Glass posts are then placed in the master to define reservoirs for liquids. Uncured PDMS is cast over the master and cured. This is achieved by heating the PDMS to around 65° C. for 1 hour. After curing, the PDMS is removed from the master and the glass posts are removed. In order to seal the channels a second, flat layer of PDMS is used. Both PDMS elements are oxidised and then brought into contact. The oxidation converts $—OSi(CH_3)_2O—$ groups at the surface to $—O_nSi(OH)_{4-n}$. This is believed to result in the formation of bridging, covalent siloxane (Si—O—Si) bonds, which forms an irreversible seal between the PDMS layers.

Duffy et al also state that PDMS seals irreversibly to glass, silicon, silicon oxide, quartz, silicon nitrate, polyethylene, polystyrene and glassy carbon after cleaning and exposing both surfaces to an oxygen plasma.

The method laid out in Duffy proposes a means of manufacture of microfluidic devices in under 24 hours. Reduction in the time taken to make the devices is limited by the time taken to mould and cure the elastomer.

In contrast to PDMS devices, thermoplastic microchannels can be made in a matter of seconds due to the high throughput injection moulding techniques available. However, the sealing means for such channels are not so sophisticated. The techniques used (thermal annealing, adhesive tape, solvent bonding) all tend to deform the microstructures and often introduce materials unsuitable for the intended application, such as toxic solvents or highly autofluorescent adhesives. Moreover, as these materials are inflexible, mechanical pumping is not possible and other techniques, such as electro-osmotics, must be relied on.

WO02/43615 discloses the bonding of an elastomer to a non-elastomer substrate containing recesses which form microfluidic channels. This can be done by creating microchannels in the substrate using traditional methods, filling the channels with sacrificial material, coating the substrate with uncured elastomer, curing the elastomer and finally removing the sacrificial material. However, this technique still includes a time delay while the elastomer is cured.

Other bonding methods disclosed use Van der Waals, covalent and ionic bonds. Covalent bonding is described in relation to the bonding of glass to a silicone elastomer and requires the glass substrate to first be exposed to agents such as vinyl silane or aminopropyltrithoxy silane. The other examples given also relate to glass substrates which, as mentioned previously, are not suited to the field of biomedical applications.

Therefore there still exists a need for a cheap, easy to manufacture microfluidic structure which is suited to use in the biomedical and biochemical fields.

SUMMARY

According to a first aspect the present invention provides a microfluidic structure comprising a thermoplastic portion defining a microfluidic recess, a bonding layer on the thermoplastic portion and a siloxane elastomer portion covalently bonded to the bonding layer to seal the microfluidic recess.

By sealing the microfluidic recess a microchannel or series of microchannels are created.

Such a microfluidic structure combines the virtues of elastomer technology with those of high-throughput compact disc injection moulding. The microfluidic recess can be formed simply, quickly and cheaply using known injection moulding techniques, which are not hampered by the need for a curing step. However the positive qualities associated with elastomers can be brought to the structure by using this to seal the microchannels.

The inventors have realised that a microfluidic device containing these advantageous properties can be created by coating a thermoplastic portion with a bonding layer that is capable of forming a covalent bond with siloxane elastomer when activated.

While various siloxane elastomers can be used to form the covalent bond, it is preferable that PDMS is used.

The bonding layer can take a number of forms, but preferably the bonding layer is formed from silica. The silica and elastomer can then be oxidised and brought into contact to form an irreversible bond. An advantage of this method of bonding is that no external pressure needs to be applied during the bonding step, which prevents the sagging and structural deformation that can occur in other, more forceful methods of bonding. The bonding between the silica and elastomer is stronger than the tensile strength of the elastomer, such that peel off tests result in the fracture of the elastomer and not the $SiO_2$/plastic interface. In tests it has been found that bonding in this manner between silica and PDMS is capable of withstanding a tension of at least $30N/cm^2$ before fracture.

The silica is preferably activated by oxygenation, preferably achieved by oxygen plasma under low pressure or at atmospheric pressure by a corona surface treater.

Preferably the layer of silica is approximately 300 nm thick as this allows for the subsequent use of surface modification techniques well established in relation to glass microfluidic structures (such as well known silanisation chemistry). As mentioned above, the first microfluidic devices were manufactured using glass and therefore there is a large body of work detailing how to adapt or treat glass microchannels for use in different applications. By depositing silica over the thermoplastic portion this knowledge can be applied to the microfluidic structures of the present invention. Thinner silica layers of 100 or 200 nm can also be provided.

Viewed from another aspect the present invention provides a microfluidic structure comprising a thermoplastic portion defining a microfluidic recess, a layer of silica on the thermoplastic portion, and a PDMS portion covalently bonded to the silica layer such that it seals the microfluidic recess.

The microfluidic recess can take any shape necessary in order to carry out the desired function and can be created using any of the known techniques for moulding thermoplastics.

Various thermoplastics can be used in the invention, thus allowing the user to select the optimal material for a given application based on, e.g. chemical and optical properties or on price. However, the invention has been found to work particularly well with cycloolefin copolymer (Zeonor), polycarbonate and poly(methylmethacrylate) (PMMA). Zeonor is particularly attractive for fluorescence applications since its autofluorescence levels are similar to those of glass.

While the device can simply consist of a thermoplastic portion and an elastomer layer bonded together, it is possible for the layer of elastomer to also be coated onto another material, such as another thermoplastic portion having a microfluidic recess. This results in the elastomer portion forming a flexible membrane separating channels in two thermoplastic portions, e.g. polymer chips. By applying pressurised air to an upper-layer channel, the control channel, the membrane is deflected downwards, influencing the fluid in the lower channel, the flow channel. A single control channel can be used as a valve, to selectively allow and prevent flow in the flow channel, or a number of control channels can be used to pump fluid along the flow channel. Using a microfluidic structure according to the present invention improves the mechanical properties of the actuating channels as only a single wall of each channel is flexible. Undesired wall distortion is thus avoided, and the force from the pressurised air is transferred more efficiently to the membrane than in chips made of elastomer only.

According to another aspect the present invention provides a method of manufacturing a microfluidic structure comprising the steps of providing a thermoplastic portion having a microfluidic recess, depositing a layer of silica on the thermoplastic portion, oxidising the silica layer and bringing the oxidised layer of silica into contact with an oxidised portion of PDMS to create a covalent bond.

Preferably the bonding step does not involve external pressure, thus preventing distortion of the channels during manufacture.

Preferably the master used for injection molding of the thermoplastic portion is fabricated by silicon dry etching. This may be used to make a microfluidic recess or recesses, e.g. channels, with rectangular cross sections. Therefore when the PDMS layer is deflected into the channel only the central part of the flow channel floor is brought into contact with the PDMS layer. Even though the closure is incomplete, the reduction in cross sectional area still achieves the desired pumping effect. However, in order to improve valve closure, it is preferable that the master used for thermoplastic molding is manufactured using isotropical etching techniques in order to create channels with an arched cross section in the thermoplastic portion.

Preferably the PDMS is formed by spin coating of uncured polymer onto a backing layer, such as Zeonor support film. This backing layer can be peeled off after curing or left in place depending on the application for which the microfluidic structure will be used. More preferably however, the PDMS layer is created by spraying the uncured elastomer onto a backing layer as this simplifies the process.

The manufacture and use of a silica layer on a thermoplastic portion having a microfluidic recess is itself advantageous in that such a thermoplastic portion is then available to have its microfluidic recess sealed to create a microfluidic platform and in addition the channels can be modified in accordance with well known techniques.

According to another aspect the present invention therefore provides a thermoplastic portion having a microfluidic recess in its upper surface and a layer of silica deposited on the upper surface.

Preferably the silica layer is thick enough for standard glass surface modification techniques to be applied. Preferably the silica layer at least 300 nm thick. So that modifications can be applied on all surfaces of the portion it is preferable that a silica layer is deposited on all surfaces of the thermoplastic portion.

According to a further aspect the present invention provides a method of preparing a thermoplastic portion, comprising forming a microfluidic recess in its upper surface and depositing a layer of silica on the upper surface.

In one preferred method the silica layer is deposited on the thermoplastic portion by electron beam evaporation. This technique is known in the field of optics, for modifying optical properties, but has not previously been used in the field of microfluidics, where the silica is instead used for bonding purposes. Another standard method used in optics that can be used to deposit silica onto the thermoplastic portion is chemical vapour deposition. In another preferred method the silica layer is formed by liquid phase deposition. This reduces the manufacture time of the device as it eliminates the time consuming vacuum pumping of an evacuation chamber. In addition this results in the whole portion being coated with silica, which allows each side of the thermoplastic portion to be covalently bonded. In order to achieve the same effect using electron beam or chemical vapour deposition the deposition step would have to be repeated several times with the thermoplastic portion positioned at different angles. Also, when using liquid phase deposition all the sides of the recess are be coated, which can be beneficial in some applications.

Employing the method of liquid phase deposition in the field of microfluidics is inventive in its own right and therefore, viewed from another aspect the invention provides a method of manufacturing a microfluidic structure comprising the steps of forming a substrate having a microfluidic recess and depositing a layer of silica on the substrate by liquid phase deposition.

Microfluidic structures in accordance with the present invention can be used in many different applications, but they are particularly suited for use in fluorescence detection (wherein, for example, the fluorescence is provided by labeled cells or concatemeric DNA molecules), cell culture and in the construction of valves and pumps.

BRIEF DESCRIPTION OF THE DRAWING

A preferred embodiment will now be described, by way of example only, with reference to the accompanying drawings, in which:

FIGS. 5A-E show a further example of a process of forming a microfluidic device according to the present invention;

FIG. 6 shows a cross section through the finished microfluidic device created by the process shown in FIGS. 5A-E;

FIG. 10 shows optical cross sections through a completed device according to the present invention.

DETAILED DESCRIPTION

Figure 1:
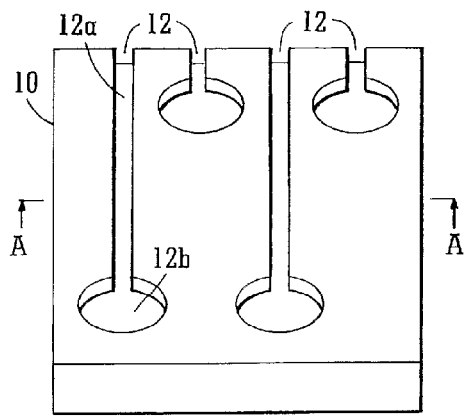
FIG. 1 shows a thermoplastic portion having a microfluidic recess in accordance with the present invention.

FIG. 1 shows a thermoplastic portion 10 after injection moulding to create microfluidic recesses 12. These consist of a narrow channel 12a and larger reservoirs 12b for storing liquid. These recesses 12 are formed on the thermoplastic portion 10 by injection moulding using standard compact disc (CD) moulding technology. Numerous chips can be moulded on a single CD after which each chip is diced out.

Figure 2A:
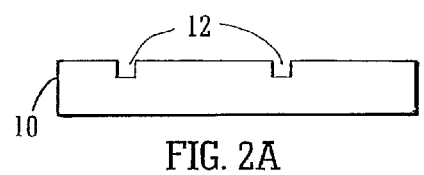
FIGS. 2A-D show a process of forming a microfluidic device according to the present invention as shown in relation to a cross section along line A-A of FIG. 1.
Figure 2B:
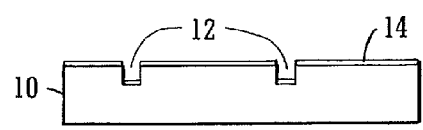

Thermoplastic portion 10 is also shown in FIG. 2A in cross section along the line A-A. In order to seal recesses 12, a layer of silica 14 is deposited on the upper side of thermoplastic portion 10. This is achieved by electron beam evaporation.

In a separate process a layer of PDMS is prepared by spin coating uncured PDMS onto a support film (see FIG. 5C). The PDMS is then cured to form a solid layer of PDMS 16. This can be carried out a location and time remote from the thermoplastic chip manufacture and the cured PDMS stored until such time as it is needed. Therefore the curing time does not interfere with the manufacturing time of the microfluidic structure.

Figure 2C:
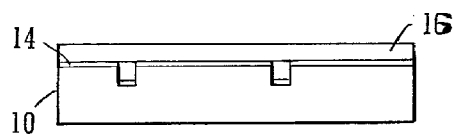

When it is desired to join the thermoplastic portion 10 and PDMS layer 16 together, the silica layer 14 and the PDMS layer 16 are oxidised. They are then brought into contact with no external pressure and form a covalent irreversible bond, as shown in FIG. 2C.

Figure 2D:
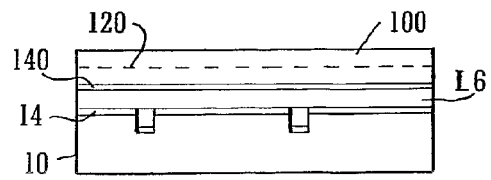

If desired a further thermoplastic portion 100 can be attached to the other side of PDMS layer 16, again using an oxidised silica layer 140 and oxidizing the other side of the PDMS layer 16. This is shown in FIG. 2D. By forming the second thermoplastic layer 100 with microfluidic recesses 120 (shown in phantom) and positioning these perpendicular to those of the first thermoplastic portion 10, valves and pumps can be created. Such a thermoplastic layer 100 can thus act as a control chip, wherein pressurised air pumped into recesses 120 control the flow of fluid in microfluidic recesses 12. This type of device is described in more detail in relation to FIGS. 8A-C.

Figure 3A:
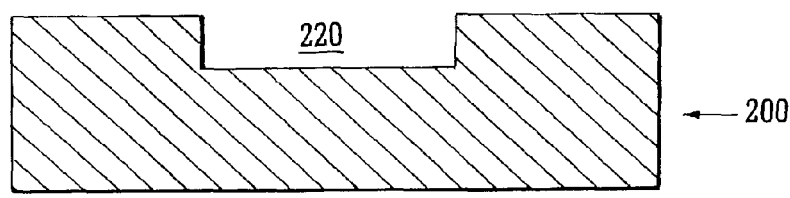
FIGS. 3A-D show a process of forming a microfluidic device according to the present invention.
Figure 3B:
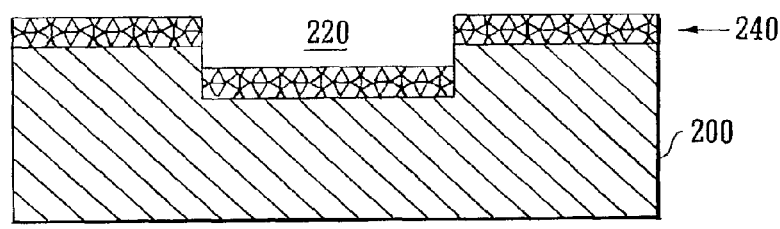
Figure 3C:
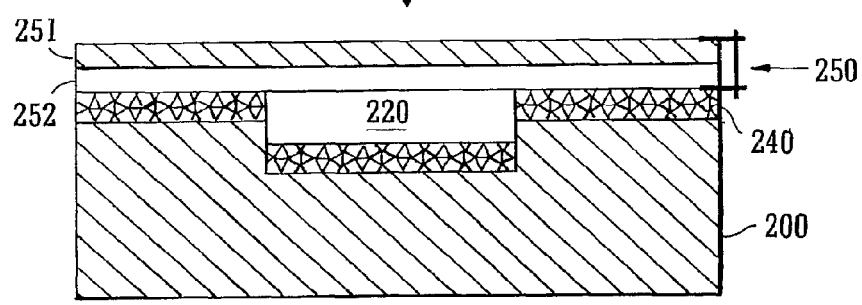
Figure 4A:
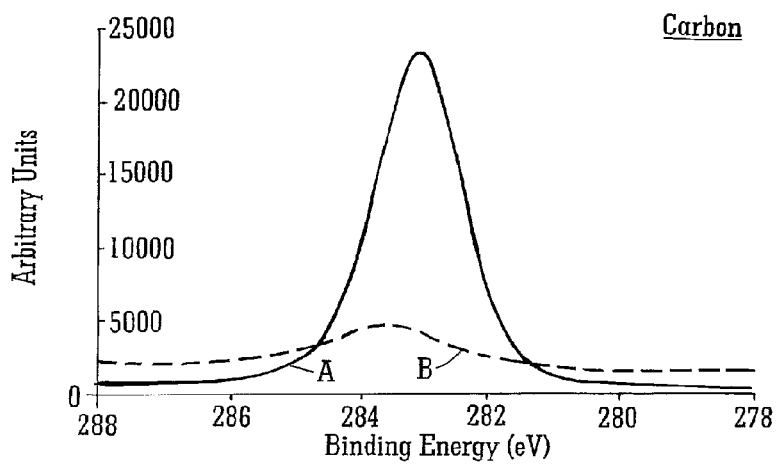
FIGS. 4A-C show Electron Spectography for Chemical Analysis (ESCA) data both before and after disposition of a silica layer on a thermoplastic portion.
Figure 4B:
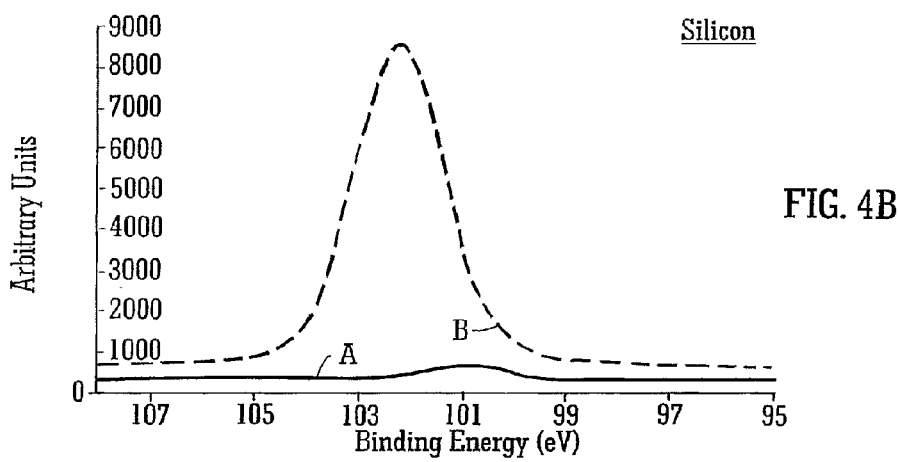
Figure 4C:
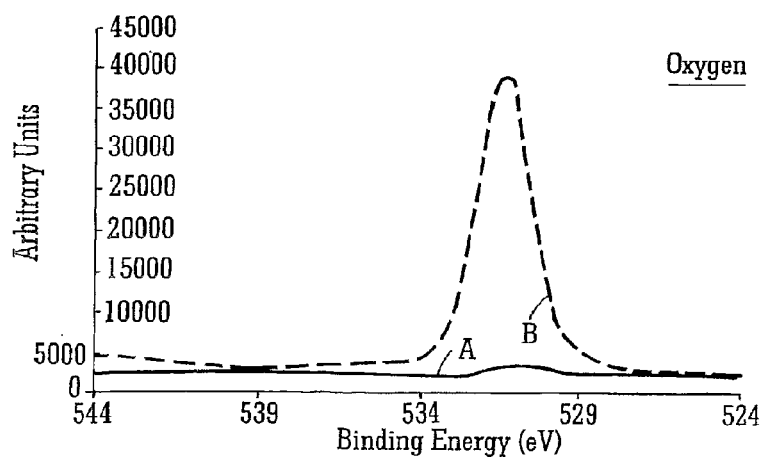

FIGS. 3A-C show this process again in relation to a thermoplastic portion 200 comprising only a single microchannel 220. Thermoplastic portion 200 is manufactured as previously described. A layer of silica 240 is then deposited on the top surface of the thermoplastic portion 200 using electron beam deposition, although other methods can also be used. FIGS. 4A-C show the ESCA data obtained from a surface analysis of the thermoplastic portion 200 before (line A) and after (line B) silica deposition. It can clearly be seen that the carbon of the thermoplastic portion is covered by the silica leaving a surface layer rich in silicon and oxygen.

This silica deposition results not only in a layer of silica 240 on the top of the microstructure 200 but also a layer in the microchannel 220 itself. This allows well known glass treatment techniques to be applied to the microchannel 220.

Figure 3D:
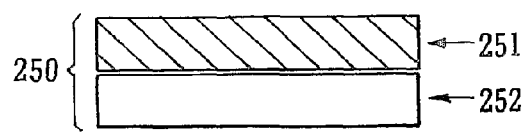

As shown in FIG. 3D a lid 250 is created comprising a support film 251 of thermoplastic material (e.g. Zeonor) and a Layer of siloxane elastomer 252 (e.g. PDMS).

In order to bond the lid 250 to the thermoplastic portion 200 both components are oxidised and then placed in contact with each other, see FIG. 3C. Without the need to apply external pressure a covalent bond is created sealing the microchannel 220.

FIG. 5A shows that the thermoplastic portion 200 is diced from an injection moulded CD 20 created using well known techniques. In FIG. 5B the step of silica deposition is shown. This results in a thin coating 240, approximately 300 nm, being formed on the top surface of the portion 200.

FIG. 5C shows the creation of the lid 250 using spin or spray coating to create a layer of PDMS 252 on a Zeonor support sheet 251. This can then be diced into appropriate sizes for attaching to the microstructures.

In order to bond the components together a surface of the PDMS layer 252 and the silica coated side of the microstructure 200 are oxidised and then placed in contact with each other. The finished product is shown in FIG. 5E. A cross section taken along plane A is shown in FIG. 6 in which the different layers of the structure can clearly be seen.

Figure 7:
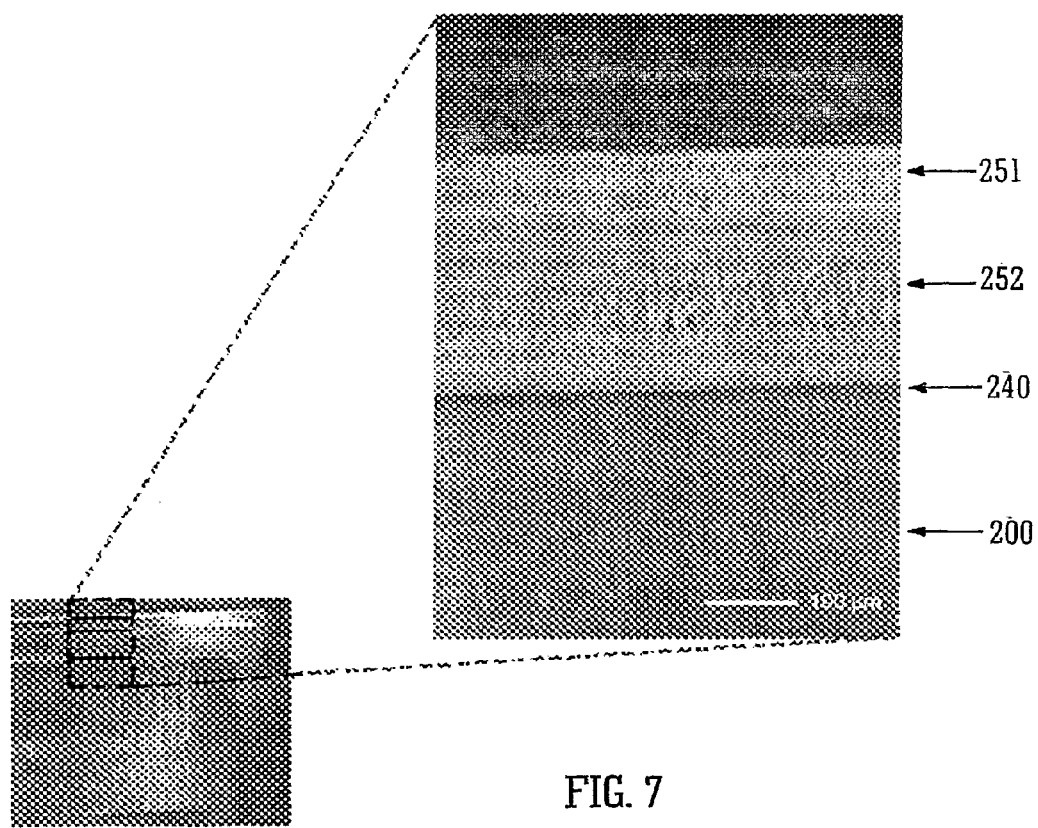
FIG. 7 shows a side view of a microfluidic chip composition in accordance with the present invention.

FIG. 7 shows these layers photographically. Again the thermoplastic portion 200 is shown with a thin layer of silica 240 attached to a PDMS lid 252 which in turn is attached to a support film 251, which can be removed if necessary.

One occasion in which the support film 252 is removed is when the device is intended for use as a pump chip. The process of making such a chip is shown in FIGS. 8A-C.

Figure 8A:
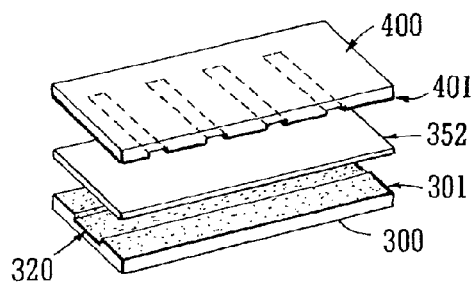
FIGS. 8A-C show the construction of a microfluidic pump device in accordance with the present invention.
Figure 8B:
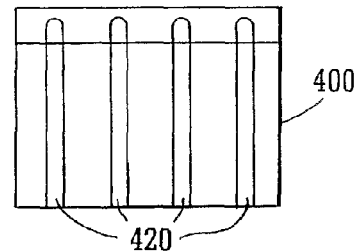
Figure 8C:
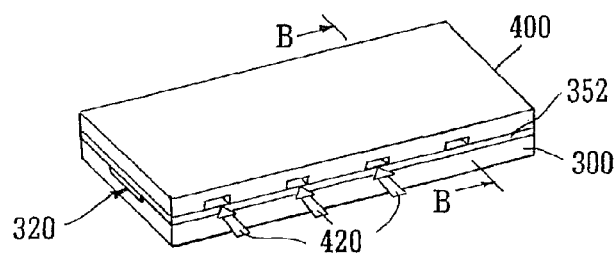

FIG. 8A shows a standard thermoplastic portion 300 of the type described in relation to FIGS. 3A and 4A having a single flow channel 320. A second thermoplastic portion 400 is also provided. This is shown in FIG. 8B and comprises of a number of separate flow channels 420 which are arranged to be perpendicular to the flow channel 320 of portion 300 in the completed chip. Both of these portions 300, 400 have a silica layer deposited on the surface 301, 401 in which their respective channels are located. A siloxane membrane 352, as created in accordance with FIG. 5C but with the support film removed, is sandwiched between the two portions 300, 400 to create a flexible membrane. The upper and lower surfaces of the siloxane membrane 352 and the silica coated layers 301, 401 of thermoplastic portions 300, 400 are oxidised and bonded together to create the completed pump chip shown in FIG. 8C.

Figure 9A:
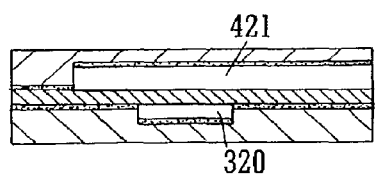
FIGS. 9A and B show a cross section through the completed device created by the process FIGS. 8A-C.
Figure 9B:
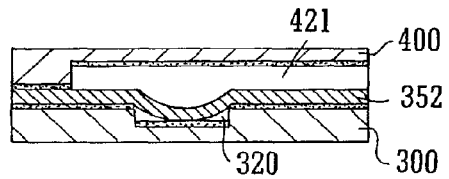

A cross section of this completed chip taken along plane B is shown in FIGS. 9A and 9B. In the open mode the pump, or control, channel 421 is not distorted by pressurised air and so the flow channel 320 is left open. When pressurised air is pumped into the pump channel 421 the siloxane layer 352 above the flow channel is distorted into the flow channel 320, preventing the flow of fluid along this path. By operating the pump channels in sequence material can be pulsed along the flow channel 320. While the rectangular flow channel 320 can be adequately closed by this method it is also possible to create curved flow paths that allow a more complete closure to be created.

FIG. 10 shows a completed microfluidic structure 500 having a number of channels and reservoirs. Optical cross sections were taken through the structure 500 at the positions indicated (I, II, III). The channels were filled with 10 micromolar of the fluorescent substance Cy5 followed by washing with distilled water. Confocal z-sectioning was performed using a Carl Zeiss LSM 5 META confocal microscope (10×/0.45 NA Carl Zeiss Plan-apochromat objective). Twenty slices spaced 7.8 micrometer apart in the z-axis was scanned generating a 156 micrometer thick stack of images, the pinhole was set to 50 resulting in an optical slice of <5.8 micrometer. A HeNe laser of 633 nm was used for excitation and emission was collected using a 650 nm long pass filter.

This resulted in an x/z image of 1300×156 micrometer covering the top and bottom of the microchannel. The results show an upper thin line corresponding to the elastomer lid and a lower line representing the thermoplastic chip. In the first cross section I the lines are broken, indicating the different microchannels. In each of these cross sections it can be seen that the lines are parallel. indicating that no sagging of the lid has occurred. This is true even in the middle of the channel (seen at cross section III). This result is achieved as no external pressure is required to bond the lid to the chip.

Figure 11:
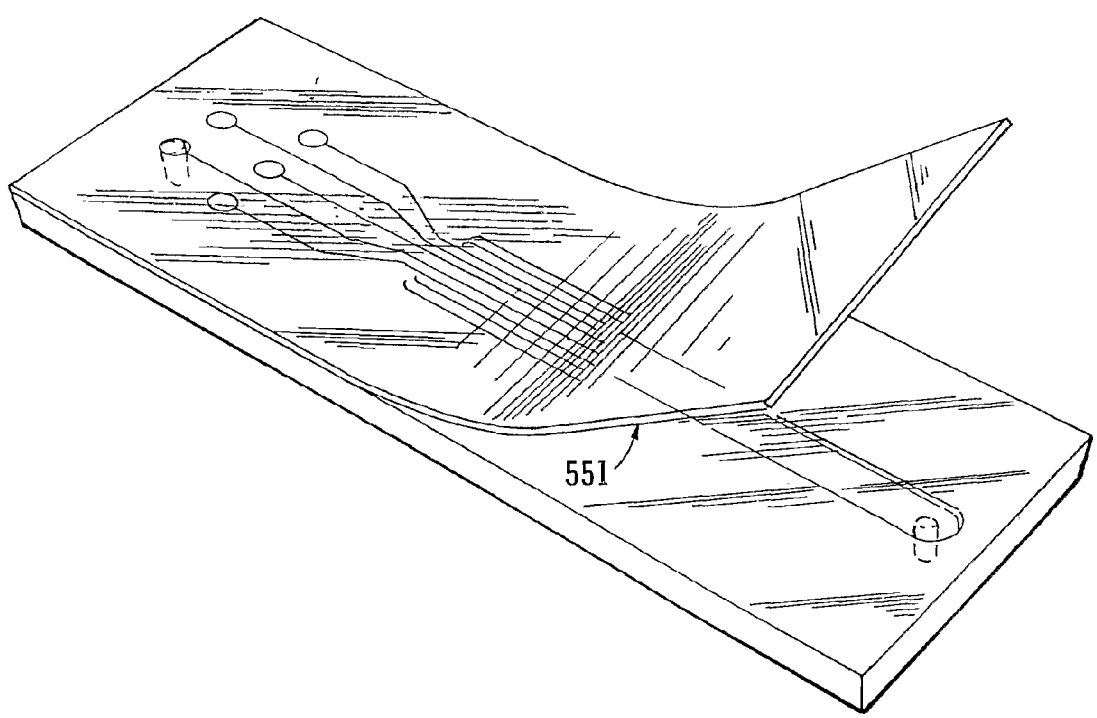
FIG. 11 shows how the support layer can be removed form this chip if required.

FIG. 11 provides an illustration of how the support film 551 used during the creation of the PDMS layer can be removed if necessary, for example in order to create the pump device shown in FIG. 8C. Alternatively this layer can be retained on the chip, as for example in optical detection.

Example 1

System Fabrication

Microstructures were designed in L-Edit Pro (Tanner EDA, Pasadena, Calif., USA). Master fabrication and compact disc injection molding were performed by Åmic AB (Uppsala, Sweden). Connection holes were drilled and the desired structures were diced out. The plastic chips were rinsed in ethanol and blown dry with nitrogen. $SiO_2$ was deposited on the chips in an Edwards 306 ED 3 electron beam evaporation chamber, resulting in an approximately 300 nm thick layer (filament current: 60 mA, acceleration voltage: 5.58 kV, pressure 3.6×10−6 mbar). The chamber temperature during deposition is well below the glass transition temperature for most thermoplastics. An atomic force microscope (Nanoscope III, Digital Instruments) operated in contact mode was used for surface topology imaging. PDMS (Elastosil RT 601, Wacker) prepolymer and curing agent were mixed at 10:1 and degassed. The uncured PDMS was spin-coated onto an 85 μm thick Zeonor support film (Nippon Zeon Co, Japan). A rotational speed of 1000 rpm resulted in an approximately 110 μm thick PDMS film, followed by curing at 70° C. for 1 hour. A Corona surface treater (Model ED-20, Electo-Technic Products, Illinois, USA) was used to oxidize the surfaces to be bonded. The electrode was swept back and forth 3 mm above the $SiO_2$ coated surface of the plastic chips for one minute, and over the PDMS film for 30 sec. The two surfaces were brought in contact and left for 10 min at 60° C. with no external pressure. Tensile tests were performed by an Instron 5544 load frame (Instron, Canton, Mass.). The support film was left in place for optical applications, but peeled off for cell culture and actuator applications.

Fluid Pumping

Chips for fluid pumping ware fabricated by sandwiching the oxidized elastomer film (approximately 110 μm) between two oxidized silica coated Zeonor chips, one representing a flow channel chip and the other one a control channel chip. All channels had a depth of 15 μm. Four control channels (width 200 μm) were oriented perpendicular to the flow channel (width 1800 μm). Pumping was also performed using 200 μm wide channels, resulting in similar flow velocities. Pressurized air (35 psi), modulated by computer-controlled three-way switch valves (LHDA 1211111H; Lee Valve, Westbrook, Conn., USA), was connected to the channels of the control chip. A 16-channel relay output board (PCLD 785, ELFA, Sweden), driven by a digital in/out board (Advantec PCI 1751, ELFA, Sweden), was employed for valve control. Dedicated software, written in Visual Basic 6 (Microsoft), was developed for hardware management. Pressurized air was applied sequentially to the control channels in each pump cycle. A typical cycle time was 500 ms with 100 ms lag time between adjacent control channels and 200 ms inter-cycle time. A suspension of fluorescent microbeads (Molecular probes, Eugene, Oreg.) was pumped through the channel and the particle movement was observed by fluorescence microscopy (Zeiss Axiovert). The volumetric flow rate was calculated from the linear velocity of the fluorescent microbeads.

Cell Culture

Sealed chips with the support film removed were sterilized in ethanol and thoroughly rinsed with cell culture medium. Chinese hamster ovary (CHO-KI) cells tranfected with an enhanced green fluorescent protein plasmid (Clontech) were removed from the tissue culture vessels by trypsin treatment. The resuspended cells were washed in cell culture medium (RPMI 1640 with 10% FBS and penicillin/streptomycin), and injected in the microchannels using a syringe. The chips were immersed in a Petri dish containing cell culture medium and incubated at 37° C. with 5% $CO_2$. Chips were transferred to a Petri dish containing fresh medium after 72 hrs. Cell viability, adhesion and growth were monitored for seven days by removing one chip every other day, for examination by fluorescence microscopy.

Cell Counting

Mononucleated cells were purified from peripheral blood by Ficoll separation and resuspended in PBS (137 mM NaCl, 2.7 mM KCl, 10 mM phosphate buffer, pH 7.4). The cells were stained by anti-CD19 PE+anti-CD3 FITC, anti-CD4 PE+anti-CD8 FITC, or with anti-CD20 FITC+anti-CD4 PE (Dako). The three different stained lymphocyte samples were pumped through three parallel microchannels (50×40 μm cross section.) with a syringe pump PHD-2000 (Harvard instruments) at a rate of 1 μL/min. A confocal microscope (Zeiss LSM 5 META) operated in line-scanning mode, across all three channels perpendicular to the direction of liquid flow, was used to detect the cells. The microscope focus was set to the center of the microchannels and the pinhole was set to 400 μm corresponding to a calculated optical slice of <5 μm. Typically 10000 lines of 512 pixels were recorded, with a voxel time of 1.6 microseconds, resulting in a data acquisition time of approximately 10 seconds. The line scan data were stored in an 8-bit/channel rgb-TIF-file and analyzed by dedicated software written in MATLAB 6.5 (MathWorks, Mass.). The data obtained was verified by flow cytometry using a FacSORT instrument (Becton Dickinson).

Therefore the present invention provides an efficient means for large scale, inexpensive production of disposable microfluidic chips with integrated actuators. The microfluidic structures of the present invention support mammalian cell growth and have excellent optical properties for fluorescence detection.

What is claimed is:

1. A method for forming a microfluidic structure, comprising:
   (a) providing a thermoplastic portion that comprises a microfluidic recess;
   (b) generating a layer of silica on said thermoplastic portion;
   (c) subjecting said layer of silica generated in (b) to oxidation conditions to provide an oxidized layer of silica; and
   (d) subsequent to (c), bringing said oxidized layer of silica in contact with an oxidized portion of poly(dimethylsiloxane) (PDMS) to covalently bond said oxidized layer of silica to said PDMS, thereby forming said microfluidic structure, wherein bonding between said oxidized layer of silica and said PDMS is stronger than a tensile strength of said PDMS.

2. The method of claim 1, wherein (a) comprises providing an additional thermoplastic portion that comprises an additional microfluidic recess, and (b) comprises generating an additional layer of silica on said additional thermoplastic portion, and wherein said PDMS is sandwiched between said thermoplastic portion and said additional thermoplastic portion.

3. The method of claim 2, wherein (c) comprises subjecting said additional layer of silica to oxidation conditions to provide an additional oxidized layer of silica, and wherein (d) comprises bringing said additional oxidized layer of silica in contact with an additional oxidized portion of said PDMS to covalently bond said additional oxidized layer of silica to said PDMS.

4. The method of claim 3, wherein said microfluidic recess is perpendicular to said additional microfluidic recess.

5. The method of claim 3, wherein said oxidized portion of said PDMS and said additional oxidized portion of said PDMS are on opposite sides of said PDMS.

6. The method of claim 3, wherein said microfluidic recess and/or said additional microfluidic recess permit said PDMS to distort under application of pressurized air or vacuum.

7. The method of claim 3, wherein said microfluidic recess is configured to direct fluid flow along said additional microfluidic recess upon application of positive pressure or vacuum to said microfluidic recess.

8. The method of claim 3, wherein said additional thermoplastic portion comprises a plurality of microfluidic recesses.

9. The method of claim 1, wherein said thermoplastic portion comprises a plurality of microfluidic recesses.

10. The method of claim 1, wherein said layer of silica is generated using electron beam evaporation.

11. The method of claim 1, wherein said layer of silica is generated using liquid phase deposition or vapor deposition.

12. The method of claim 1, wherein said thermoplastic portion is injection molded.

13. The method of claim 1, wherein said thermoplastic portion is selected from the group consisting of cycloolefin copolymer, polycarbonate and poly(methylmethacrylate).

14. The method of claim 1, wherein said oxidized layer of silica is bonded to said PDMS without use of external pressure.

15. The method of claim 1, wherein said layer of silica is from 100 nanometers (nm) to 300 nm in thickness.

16. The method of claim 1, wherein said microfluidic structure is transparent to electromagnetic radiation.

17. The method of claim 1, wherein said microfluidic structure is usable for cell culture.

18. The method of claim 1, wherein said microfluidic recess is part of a valve of pump of said microfluidic microstructure.

19. The method of claim 1, wherein said microfluidic recess is sealed by said PDMS.

* * * * *